US012577205B2

(12) United States Patent
Umbarkar et al.

(10) Patent No.: US 12,577,205 B2
(45) Date of Patent: Mar. 17, 2026

(54) HYDROGENATION OF IMINES BY PALLADIUM BASED CATALYST

(71) Applicant: Council of Scientific and Industrial Research, New Delhi (IN)

(72) Inventors: Shubhangi Bhalchandra Umbarkar, Pune (IN); Chepuri Venkata Ramana, Pune (IN); Doke Dhananjay Shahuraj, Pune (IN); Mane Jayesh Shankar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 403 days.

(21) Appl. No.: 18/553,251

(22) PCT Filed: Mar. 29, 2022

(86) PCT No.: PCT/IN2022/050316
§ 371 (c)(1),
(2) Date: Sep. 29, 2023

(87) PCT Pub. No.: WO2022/208545
PCT Pub. Date: Oct. 6, 2022

(65) Prior Publication Data
US 2024/0208906 A1 Jun. 27, 2024

(30) Foreign Application Priority Data
Mar. 31, 2021 (IN) ............................ 202111015508

(51) Int. Cl.

| | |
|---|---|
| ***C07D 213/42*** | (2006.01) |
| ***B01J 23/44*** | (2006.01) |
| ***B01J 27/138*** | (2006.01) |
| ***B01J 27/185*** | (2006.01) |
| ***B01J 37/03*** | (2006.01) |
| ***B01J 37/08*** | (2006.01) |

(52) U.S. Cl.
CPC ............ *C07D 213/42* (2013.01); *B01J 23/44* (2013.01); *B01J 27/138* (2013.01); *B01J 27/1856* (2013.01); *B01J 37/035* (2013.01); *B01J 37/08* (2013.01)

(58) Field of Classification Search
CPC ....... C07D 213/42; B01J 23/44; B01J 27/138; B01J 27/1856; B01J 37/035; B01J 37/08
See application file for complete search history.

(56) References Cited

U.S. PATENT DOCUMENTS 6,365,745 B1 * 4/2002 Matsui .................. C07C 241/04 564/151
8,217,204 B2 * 7/2012 Maeda .................... C07B 53/00 502/166

FOREIGN PATENT DOCUMENTS

IN 6573/CHE/2014 A 7/2016
WO 2010140636 A1 12/2010

OTHER PUBLICATIONS

Dalla-Vechia et al., 11 Org. Biomol. Chem. 6806 (2013) (Year: 2013).*
David Lennon et al, Org. Process Rev. Dev. 2019, 23, 977-989.

* cited by examiner

*Primary Examiner* — Timothy R Rozof
(74) *Attorney, Agent, or Firm* — Fox Rothschild LLP

(57) ABSTRACT

The present invention discloses a process for the hydrogenation of imines of Formula I by palladium-based catalyst to provide product of Formula II with more than 95% conversion of substrate and more than 95% of desired hydrogenated product.

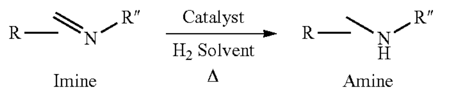

R = aliphatic/aromatic
R″ = aliphatic/aromatic

2 Claims, 5 Drawing Sheets

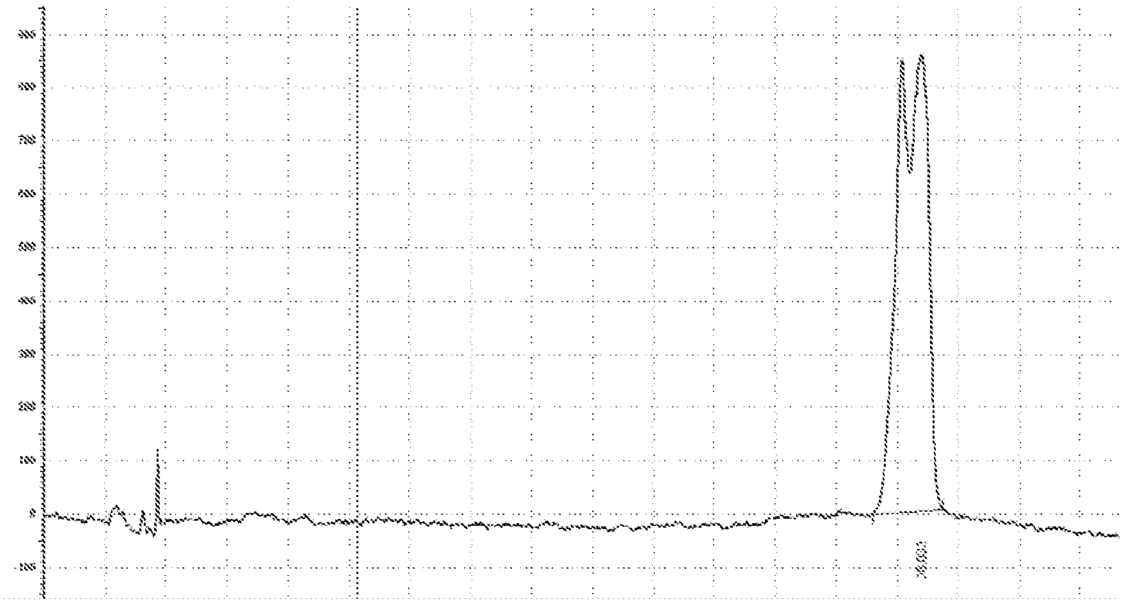
FIG. : 1

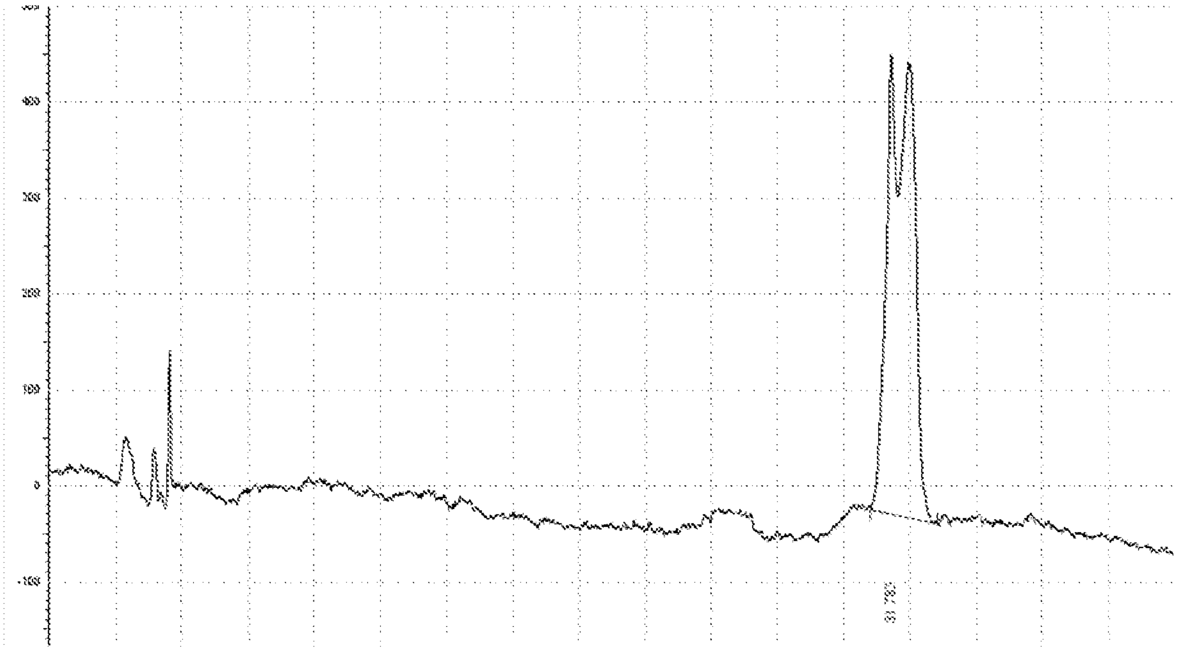
FIG. : 2

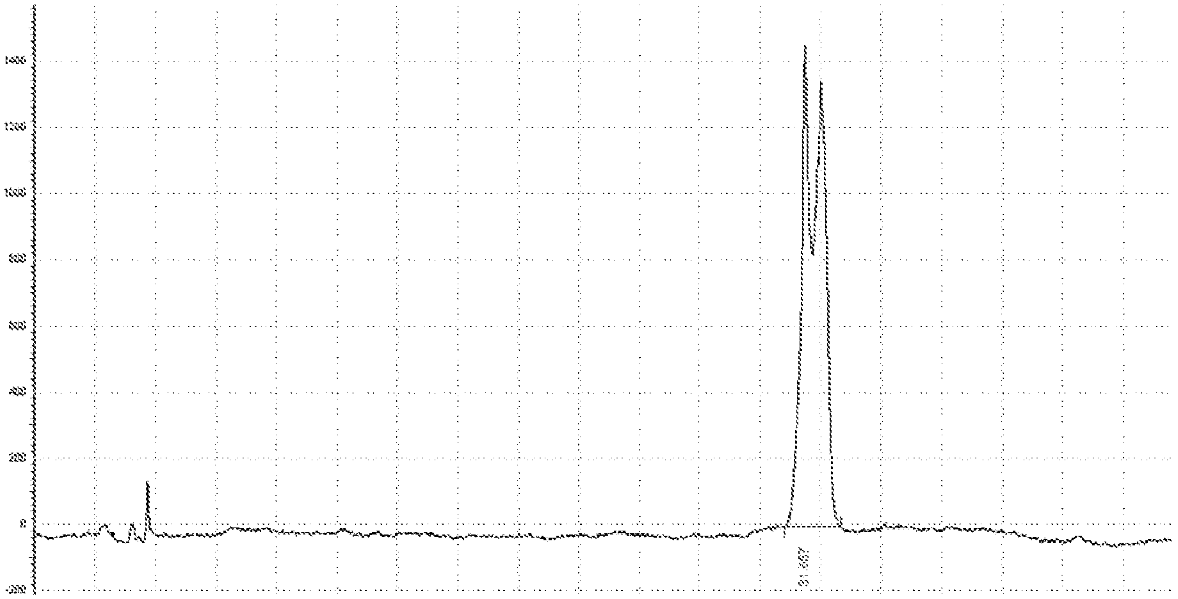
FIG. : 3

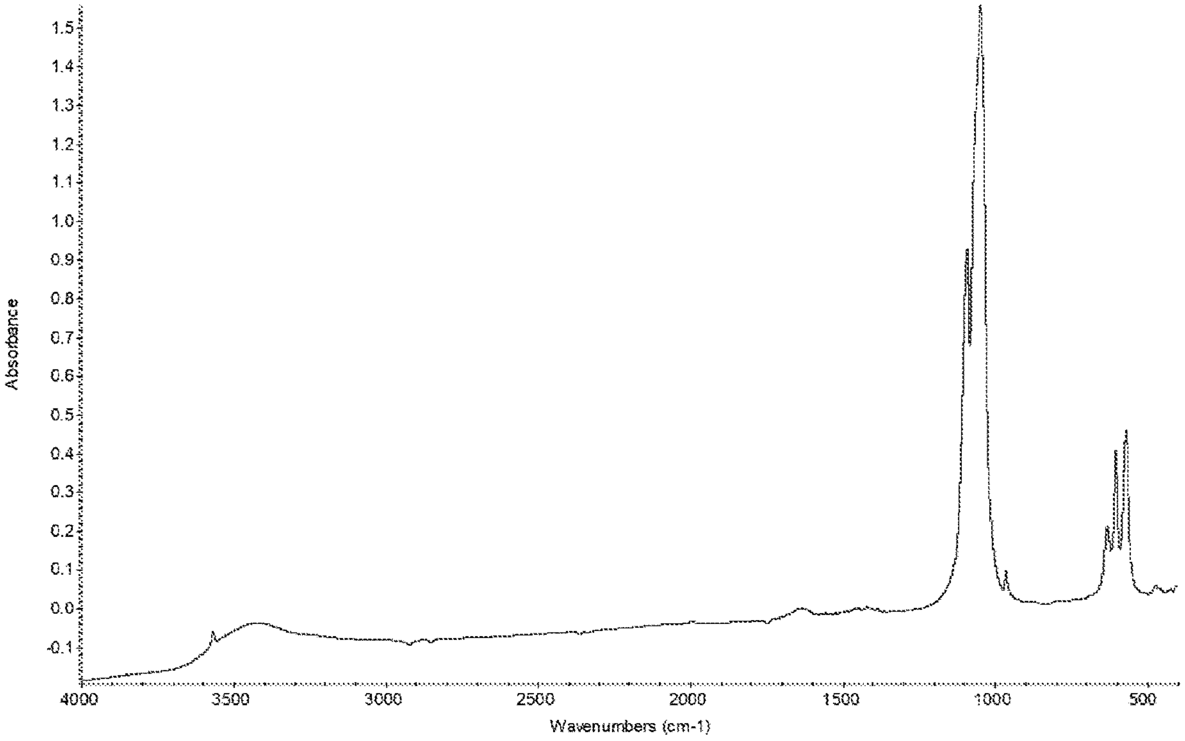
FIG. : 4

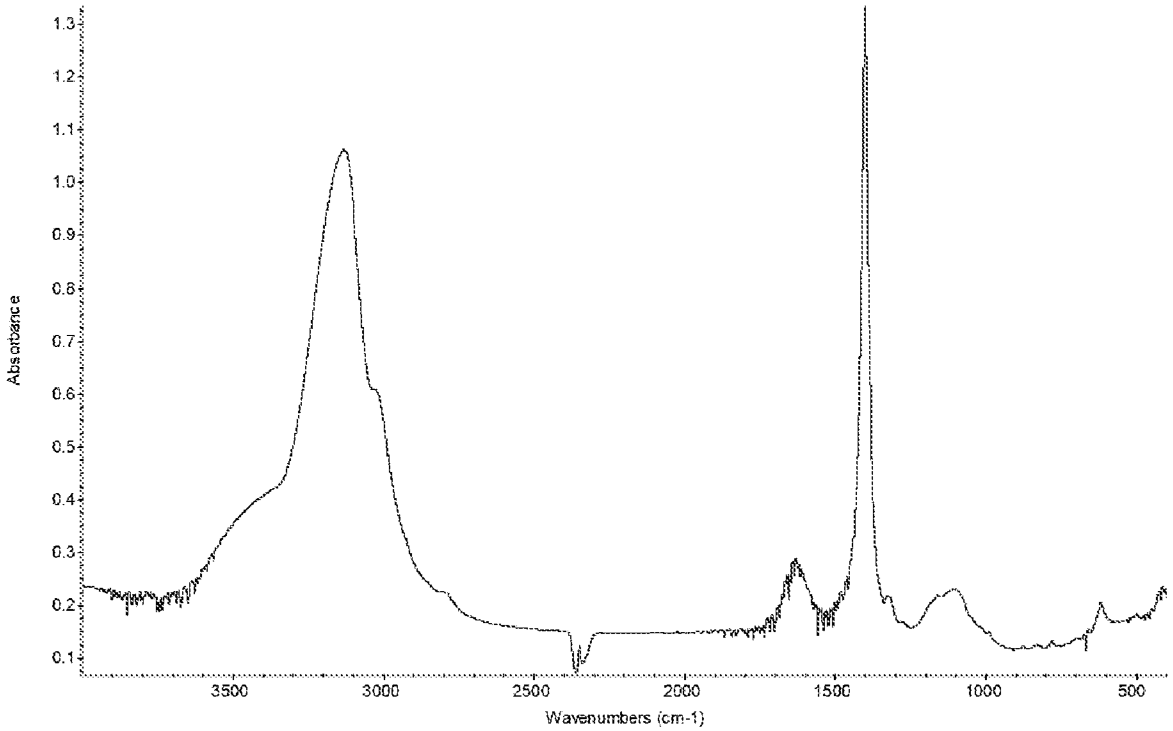
FIG. : 5

HYDROGENATION OF IMINES BY PALLADIUM BASED CATALYST

CROSS-REFERENCE TO RELATED APPLICATION

This application is a national phase filling of International Patent Application No. PCT/IN2022/050316 filed Mar. 29, 2022, which claims priority to Indian Patent Application number 202111015508 filed Mar. 31, 2021, the contents of both of which are hereby incorporated by reference.

FIELD OF THE INVENTION

The present invention relates to a process for the hydrogenation of imines of Formula I metal-based catalyst. More particularly, the present invention relates to a process for the hydrogenation of tert-butyl(Z)-2-(4-(pyridin-2-yl)benzylidene) hydrazine-1-carboxylate of Formula IA by palladium based catalyst, especially palladium supported on basic support.

BACKGROUND AND PRIOR ART OF THE INVENTION

Atazanavir drug with its salt form of sulphate is used for the treatment of HIV. The drug is synthesized from tert-butyl 2-(4-(pyridin-2-yl)benzyl)hydrazine-1-carboxylate (compound 1) as a starting material but to get this starting material initially there is an imine group which needs to be hydrogenated to get the compound 1. Hydrogenation of imine is quite a difficult part as the imines are not much stable. At the time of hydrogenation, there are chances of hydrolysis of reactant which destroys the original structure due to which the yield of the final product get reduced. There are several reagents available for the hydrogenation of imines such as $NaBH_4$, $NaBH_3CN$, $LiBH_4$, etc. however additional acidity or basicity is essential and several organic compounds e.g. trifluoroacetic acid, benzoic acid, p-toluene sulphonic acid (PTSA) have been used. Due to use of these activators separation/purification of the product becomes tedious. Comparing these reagents with the catalytic system, the catalytic system works much better than the stoichiometric reagents.

U.S. Pat. No. 6,365,745B1 discloses a method for producing a hydrazine derivative comprises reducing a hydrazone derivative in the presence of at least one base selected from the group consisting of an organic base and an inorganic base, and a metal hydrogenating catalyst. In the prior art patent both organic and inorganic base are needed for the reaction whereas in the present invention no base is required.

Reported catalysts for imine hydrogenation are based on noble metals such as palladium, platinum, gold, some transition metals like rhodium and ruthenium, in which palladium is used frequently. The higher loading of noble metal catalyst increases the cost of the process. Hence use of minimum amount of noble metal catalyst is preferred. The catalysts used for the synthesis of compound 1 are palladium based where the typically metal loading is very high (10% Pd/C) and/or harsh reaction conditions are warranted. High temperature or high pressure may lead to the formation of side products due to breaking of C—C or C—N bonds. Hence a catalyst with minimal noble metal loading working under milder conditions is 1 desirable which will give a cost effective process for production of tert-butyl 2-(4-(pyridin-2-yl)benzyl)hydrazine-1-carboxylate.

An article entitled "Hydrogenation of Benzonitrile over Supported Pd Catalysts: Kinetic and Mechanistic Insight" by David Lennon et al. and published in the journal "*Org. Process Res. Dev.* 2019, 23, 977-989" reports liquid phase hydrogenation of benzonitrile over a 5 wt % Pd/C catalyst using a stirred autoclave. The article describes hydrogenation of nitrile using Pd/C & Pd/Al2O3. C is neutral support and Al2O3 is amphoteric support. In this article nitrile hydrogenation gives toluene and ammonia due to breaking of C—N bond completely. Moreover, the catalyst used is very high (33%) with very high Pd loading (5% Pd loading) where high yield of toluene is reported instead of benzylamine due to cleavage of C—N bond due to over hydrogenation.

Therefore, there is a need in the art to develop a process for the hydrogenation of imines overcoming these drawbacks of prior art processes.

OBJECTIVES OF THE INVENTION

The main objective of the present invention is to provide a process for the hydrogenation of imines of Formula I by metal-based catalyst.

Another objective of the present invention is to provide a process for the hydrogenation of tert-butyl(Z)-2-(4-(pyridin-2-yl)benzylidene)hydrazine-1-carboxylate of Formula IA by palladium based catalyst, especially palladium supported on basic support.

SUMMARY OF THE INVENTION

Accordingly, the present invention provides a process for hydrogenation of imines by metal-based catalyst.

In an embodiment, the present invention provides a process for hydrogenation of imines of Formula I comprising reacting 0.1-2% Pd loaded catalyst on a basic support selected from $BaF_2$ and calcium phosphates with different Ca/P ratio in the range of 0.76 to 1.8 for 5-18 hours in a solvent at atmospheric pressure to 20 bar at 25° C. to 100° C. with 1 to 10 wt % catalyst loading with respect to substrate to obtain more than 95% conversion of substrate and more than 95% of desired hydrogenated product of Formula II.

Another aspect of an embodiment, the present invention provides a process for the hydrogenation of tert-butyl(Z)-2-(4-(pyridin-2-yl)benzylidene)hydrazine-1-carboxylate of formula IA to tert-butyl 2-(4-(pyridin-2-yl)benzyl)hydrazine-1-carboxylate of Formula IIA comprising reacting 0.1-2% Pd catalyst on a basic support selected from $BaF_2$ and calcium phosphates with different Ca/P ratio in the range of 0.76 to 1.8 for 5-18 hours in a solvent at atmospheric pressure to 20 bar at 25° C. to 100° C. with 1 to 10 wt % catalyst loading with respect to substrate to obtain more than 95% conversion of substrate and more than 95% of desired hydrogenated product.

ABBREVIATION $BaF_2$: Barium fluoride
Pd: Palladium
$Ba(OH)_2$: Barium Hydroxide
$Pd(OAc)_2$: Palladium(II) acetate
1% Pd/HAP1: Palladium supported by Hydroxyapatite (HAP1) (Ca:P ratio 1.8)
1% Pd/HAP2: Palladium supported by Hydroxyapatite (HAP2) (Ca:P ratio 1.56)

1% Pd/HAP3: Palladium supported by Hydroxyapatite (HAP3) (Ca:P ratio 1.3)

1% Pd/CP1: Palladium supported by calcium phosphate (CP1) (Ca:P ratio 1.04)

1% Pd/CP2: Palladium supported by calcium phosphate (CP2) (Ca:P ratio 1.09)

1% Pd/CP3: Palladium supported by calcium phosphate (CP3) (Ca:P ratio 0.76)

BRIEF DESCRIPTION OF THE DRAWINGS

FIG. 1: High Performance Liquid Chromatography (HPLC) spectrum of authentic reactant tert-butyl(Z)-2-(4-(pyridin-2-yl)benzylidene)hydrazine-1-carboxylate (IA)

FIG. 2: High Performance Liquid Chromatography spectrum of authentic product tert-butyl 2-(4-(pyridin-2-yl)benzyl)hydrazine-1-carboxylate (IIA)

FIG. 3: High Performance Liquid Chromatography spectrum of final reaction mixture of example 9

FIG. 4: Infra-Red spectrum of catalyst 1Pd/HAP1.

FIG. 5: Infra-Red spectrum of catalyst $1Pd/BaF_2$

DETAILED DESCRIPTION OF THE INVENTION

The invention will now be described in detail in connection with certain preferred and optional embodiments, so that various aspects thereof may be more fully understood and appreciated.

In an embodiment, the present invention provides a process for the hydrogenation of imines of Formula I comprising reacting 0.1-2% Pd catalyst on a basic support selected from $BaF_2$ and calcium phosphates with different Ca/P ratio in the range of 0.76 to 1.8 for a period in the range of 5-18 hours in a solvent at atmospheric pressure to 20 bar pressure at a temperature in the range of 25° C. to 100° C. with 1 to 10 wt % catalyst loading with respect to substrate to obtain more than 95% conversion of substrate and more than 95% of desired hydrogenated product of Formula II.

The imines of Formula I are selected from aldimines, and ketimines;

Formula (I)

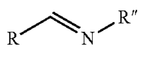

wherein R, R" are same or different, straight or branched and represents independently of each other hydrogen, $C_1$-$C_{10}$ alkyl, $C_1$-$C_{10}$ alkenyl, $C_1$-$C_{10}$ alkynyl; aryl, heteroaryl, arylalkyl, heteroarylalkyl; $C_1$-$C_{10}$ cycloalkyls, $C_1$-$C_{10}$ cycloalkenyl or cycloalkynyl.

The amine of Formula (II);

Formula (II)

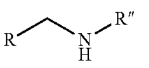

wherein R, R" are same or different, straight or branched and represents independently of each other hydrogen, $C_1$-$C_{10}$ alkyl, $C_1$-$C_{10}$ alkenyl, $C_1$-$C_{10}$ alkynyl; aryl, heteroaryl, arylalkyl, heteroarylalkyl; $C_1$-$C_{10}$ cycloalkyls, $C_1$-$C_{10}$ cycloalkenyl or cycloalkynyl.

The process of the present invention is as shown below in scheme 1:

Scheme 1

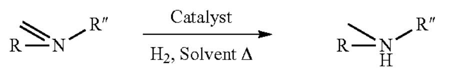

Formula I Formula II wherein R, R" are same or different, straight or branched and represents independently of each other hydrogen, $C_1$-$C_{10}$ alkyl, $C_1$-$C_{10}$ alkenyl, $C_1$-$C_{10}$ alkynyl; aryl, heteroaryl, arylalkyl, heteroarylalkyl; $C_1$-$C_{10}$ cycloalkyls, $C_1$-$C_{10}$ cycloalkenyl or cycloalkynyl.

In another aspect of an embodiment, the present invention provides a process for the hydrogenation of tert-butyl(Z)-2-(4-(pyridin-2-yl)benzylidene)hydrazine-1-carboxylate of Formula IA to tert-butyl 2-(4-(pyridin-2-yl)benzyl)hydrazine-1-carboxylate of Formula IIA comprising reacting 0.1-2% Pd catalyst on a basic support selected from $BaF_2$ and calcium phosphates with different Ca/P ratio in the range of 0.76 to 1.8 for a period in the range of 5-18 hours in a solvent at atmospheric pressure to 20 bar at a temperature in the range of 25° C. to 100° C. with 1 to 10 wt % catalyst loading with respect to substrate to obtain more than 95% conversion of substrate and more than 95% of desired hydrogenated product.

The process is as depicted in Scheme 2:

Scheme 2

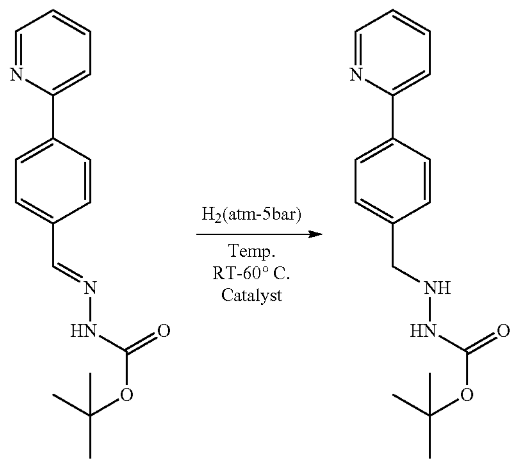

Formula IA Formula IIA

The palladium catalyst precursor is Palladium(II) acetate.

The Palladium loading is in the range of 0.1 to 0.01 wt % with respect to substrate.

The solvent is selected from methanol, iso-propyl alcohol, ethanol, ethylene dichloride, toluene, or n-hexane alone or in combination.

The present invention describes the use of Pd/BaF2 or HAP as basic support for hydrogenation of imine. In the present case specifically, basic support is used which gives high yield of the desired amine as the C—N bond breaking does not happen leading to high yield of desired product amine. Moreover, the process of the present invention does not provide over hydrogenated products and only amine is formed which is the desired product.

FIG. 1 corresponds to HPLC standard peak of tert-butyl (Z)-2-(4-(pyridin-2-yl)benzylidene) hydrazine-1-carboxylate (IA) at retention time 36.03 min.

FIG. 2 corresponds to HPLC standard peak of tert-butyl 2-(4-(pyridin-2-yl)benzyl) hydrazine-1-carboxylate (IIA) at retention time 31.78 min.

FIG. 3 HPLC spectrum of final reaction mixture of Example 9, shows peak at 31.8 min which corresponds to product tert-butyl 2-(4-(pyridin-2-yl)benzyl) hydrazine-1-carboxylate (IIA). No peak at 36 min is observed indicating complete conversion of reactant. No other peaks are observed indicating no undesired by-product formation.

FIG. 4 indicates FTIR spectrum of 1Pd/HAP1. FTIR, showed peaks at 562 $cm^{-1}$, 602 $cm^{-1}$,632 $cm^{-1}$, 962.4 $cm^{-1}$ corresponding to $PO_4$ group and 1037 $cm^{-1}$,1089 $cm^{-1}$ corresponding to stretching of P—O bond, and 3571 $cm^{-1}$ corresponding to P—OH bond confirming hydroxy appetite structure of the catalyst support. Due to low loading of Pd, no peaks corresponding to Pd were observed.

FIG. 5 indicates infrared spectrum of 1Pd/BaF2. Infrared spectrum showed peaks at 1392, 634 $cm^{-1}$ corresponding to stretching vibration of Ba—F bond, 1635 $cm^{-1}$ corresponding to stretching vibration of Ba—OH bond confirming presence of barium hydroxyl fluoride in $BaF_2$. Due to low loading of Pd, no peaks corresponding to Pd were observed.

EXAMPLES

Following examples are given by way of illustration and therefore should not be construed to limit the scope of the invention.

Example 1: Synthesis of 1% Pd/$BaF_2$

In 250 ml beaker to the slurry of 18 g $Ba(OH)_2$ in 100 ml distilled water, 5.7 g of HF (40% aqueous solution) was added drop wise. After complete addition the mixture was aged for 1 h and then heated at 100° C. to evaporate water completed till dryness. The dry powder was heated at 80° C. for 12 h now called as $BaF_2$. This dried $BaF_2$ was added to 100 ml water in a 250 ml beaker. In another 50 ml beaker $Pd(OAc)_2$ 0.211 g was dissolved in mixture of acetone: methanol (2:5 ratio) and the solution was added dropwise to the slurry of $BaF_2$. After complete addition, the mixture was stirred for additional 1 h and then heated slowly to evaporate the solvent. The solid obtained was heated at 80° C. for 12 h and then calcined at 250° C. for 5 h in an air. Resultant powder was 1% Pd/$BaF_2$.

Example 2: Synthesis of 0.5% Pd/$BaF_2$

In 250 ml beaker to the slurry of 18 g $Ba(OH)_2$ in 100 ml distilled water, 5.7 g of HF (40% aqueous solution) was added drop wise. After complete addition the mixture was aged for 1 h and then heated at 100° C. to evaporate water completed till dryness. The dry powder was heated at 80° C. for 12 h now called as $BaF_2$. This dried $BaF_2$ was added to 100 ml water in a 250 ml beaker. In another 50 ml beaker $Pd(OAc)_2$ 0.105 g was dissolved in mixture of acetone: methanol (2:5 ratio) and the solution was added dropwise to the slurry of $BaF_2$. After complete addition, the mixture was stirred for additional 1 h and then heated slowly to evaporate the solvent. The solid obtained was heated at 80° C. for 12 h and then calcined at 250° C. for 5 h in an air. Resultant powder was 1% Pd/$BaF_2$.

Example 3: Synthesis of 1% Pd/HAP1

Hydroxyapatite (HAP1) (Ca:P ratio 1.8) was synthesized by a co-precipitation method as reported by V. C. Ghantani, S. T. Lomate, M. K. Dongare, S. B. Umbarkar Green Chem., 2013, 15, 1211-1217. In a typical synthesis, the 40.297 gm calcium nitrate tetrahydrate and 13.493 gm diammonium hydrogen phosphate were dissolved separately in deionised water. Ammonia solution (25%) was added to both the solutions until the pH 12 was achieved. The calcium nitrate solution was added drop wise to the diammonium hydrogen phosphate solution with constant stirring with maintaining pH12 till complete addition. A thick white precipitate obtained was aged for 12 h and later was filtered, washed with a sufficient amount of water and dried at 120° C. for 16 h. The oven dried solid was calcined in air in a muffle furnace at 600° C. for 4 h which is called as HAP1. Then HAP1 10 g was dispersed in 100 ml water in a 250 ml beaker to make homogeneous slurry. In another beaker Pd(OAc) 0.211 g was dissolved in acetone:methanol (2:5 ratio) mixture and the resultant solution was added dropwise to HAP1 slurry. After complete addition, the mixture was additionally stirred for additional 1 h and then heated slowly to evaporate the solvent. The solid obtained was dried at 80° C. for 12 h and then calcined at 250° C. for 5 h in air. Resultant powder was called as 1% Pd/HAP1.

Example 4: Synthesis of 1% Pd/HAP2

Hydroxyapatite (HAP2) (Ca:P ratio 1.56) was synthesized by a co-precipitation method as reported by V. C. Ghantani, S. T. Lomate, M. K. Dongare, S. B. Umbarkar Green Chem., 2013, 15, 1211-1217. In a typical synthesis, the 40.297 gm calcium nitrate tetrahydrate and 13.493 gm diammonium hydrogen phosphate were dissolved separately in deionized water. Ammonia solution (25%) was added to both the solutions until the pH 10 was achieved. The calcium nitrate solution was added drop wise to the diammonium hydrogen phosphate solution with constant stirring with maintaining pH10 till complete addition. A thick white precipitate obtained was for 12 h and later filtered, washed with a sufficient amount of water and dried at 120° C. for 16 h. The oven dried solid was calcined in air in a muffle furnace at 600° C. for 4 h which is called as HAP2. Then HAP2 10 g was dispersed in 100 ml water in a 250 ml beaker to make homogeneous slurry. In another beaker Pd(OAc) 0.211 g was dissolved in acetone:methanol (2:5 ratio) and was added dropwise to HAP2 slurry. After complete addition, the mixture stirred for additional 1 h and then heated slowly to evaporate the solvent completely. The solid obtained was dried at 80° C. for 12 h calcined at 250° C. for 5 h in air. Resultant powder was called as 1% Pd/HAP2

Example 5: Synthesis of 1% Pd/HAP3

Hydroxyapatite (HAP3) (Ca:P ratio 1.3) was synthesized by a co-precipitation method as reported by V. C. Ghantani, S. T. Lomate, M. K. Dongare, S. B. Umbarkar Green Chem., 2013, 15, 1211-1217. In a typical synthesis, the 40.297 g calcium nitrate tetrahydrate and 13.493 g diammonium hydrogen phosphate were dissolved separately in deionised water. Ammonia solution (25%) was added to both the solutions until the pH 7 was achieved. The calcium nitrate solution was added drop wise to the diammonium hydrogen phosphate solution with constant stirring with maintaining pH 7 till complete addition. A thick white precipitate obtained was kept for aging for 12 h and later was filtered, washed with a sufficient amount of water and dried at 120° C. for 16 h. The oven dried solid was calcined in air in a muffle furnace at 600° C. for 4 h which is called as HAP3. Then HAP3 10 g was dispersed in 100 ml water in a 250 ml beaker and stirred to make homogenous slurry. In another beaker Pd(OAc) 0.211 g was dissolved in acetone:methanol (2:5 ratio) and added dropwise to HAP3 slurry. After complete addition, the mixture was stirred for additional 1 h and then heated slowly to evaporate the solvent completely and the solid obtained was dried at 80° C. for 12 h and calcined at 250° C. for 5 h in air. Resultant powder was called as 1% Pd/HAP3.

Example 6: Synthesis of 1% Pd/CP1

Calcium phosphate CP1 was prepared by reported method V. C. Ghantani, M. K. Dongare, S. B. Umbarkar RSC Adv., 2014, 4, 33319-33326. In a typical synthesis of CP-1, calcium nitrate (36.95 g) and diammonium hydrogen phosphate (13.8 g) were dissolved separately in 125 ml deionised water each. Initially the pH of both the solutions was adjusted to 8 by addition of ammonium hydroxide solution (5% aqueous). $NaH_2PO_4$ (3.39 g) dissolved in 25 ml deionised water was added to the diammonium hydrogen phosphate solution. Calcium nitrate solution was added drop wise to the above mixture of phosphate precursors with constant stirring (700 rpm) at 28° C. As the precipitation proceeds decrease in pH was observed. A thick white precipitate formed was aged for 12 h then filtered, washed with water and dried in an oven at 120° C. for 12 h. The dried solid was calcined at 600° C. for 4 h. The solid obtained was referred as CP1. Then CP1 10 g was dispersed in 100 ml water in a 250 ml beaker and stirred till formation of homogenous slurry. In another beaker Pd(OAc) 0.211 g was dissolved in acetone:methanol (2:5 ratio) mixture and added dropwise to CP1 slurry. After complete addition, the mixture was stirred for additional 1 h and then heated slowly to evaporate the solvent and the solid obtained was heated at 80° C. for 12 h and calcined at 250° C. for 5 h in air. Resultant powder was called as 1% Pd/CP1

Example 7: Synthesis of 1% Pd/CP2

Calcium phosphate CP2 was prepared by reported method V. C. Ghantani, M. K. Dongare, S. B. Umbarkar RSC Adv., 2014, 4, 33319-33326. In atypical synthesis of CP2, calcium nitrate (36.95 g) and diammonium hydrogen phosphate (13.8 g) were dissolved separately in 125 ml deionised water each. Initially the pH of both the solutions was adjusted to 8 by addition of ammonium hydroxide solution (5% aqueous). $Na_2HPO_4 \cdot 2H_2O$ (1.99 g) dissolved in 25 ml deionised water was added to the diammonium hydrogen phosphate solution. Calcium nitrate solution was added drop wise to the above mixture of phosphate precursors with constant stirring (700 rpm) at 28° C. A thick white precipitate formed was aged for 12 h then filtered, washed with water and dried in an oven at 120° C. for 12 h. The dried catalyst was calcined at 600° C. for 4 h. The solid mass obtained was called as CP2. Then CP2 10 g was dispersed in 100 ml water in a 250 ml beaker and stirred to make homogenous slurry. In another beaker Pd(OAc) 0.211 g was dissolved in acetone:methanol (2:5 ratio) mixture and added dropwise to CP2 slurry. After complete addition, the mixture was stirred for additional 1 h and then heated slowly to evaporate the solvent. The solid obtained was dried at 80° C. for 12 h and calcined at 250° C. for 5 h in air. Resultant powder was called as 1% Pd/CP2.

Example 8: Synthesis of 1% Pd/CP3

Calcium phosphate CP3 was prepared by reported method V. C. Ghantani, M. K. Dongare, S. B. Umbarkar RSC Adv., 2014, 4, 33319-33326. In a typical synthesis of CP3, calcium nitrate (36.95 g) and diammonium hydrogen phosphate (13.8 g) were dissolved separately in 125 ml deionised water each. Initially the pH of both the solutions was adjusted to 8 by addition of ammonium hydroxide solution (5% aqueous). $Na_3PO_4 \cdot 12H_2O$ (2.7 g) dissolved in 25 ml deionised water was added to the diammonium hydrogen phosphate solution. Calcium nitrate solution was added drop wise to the above mixture of phosphate precursors with constant stirring (700 rpm) at 28° C. A thick white precipitate formed was aged for 12 h then filtered, washed with water and dried in an oven at 120° C. for 12 h. The dried catalyst was calcined at 600° C. for 4 h. The solid obtained was called as CP3. Then CP3 10 g was dispersed in 100 ml water in a 250 ml beaker and stirred to make homogenous slurry. In another beaker Pd(OAc) 0.211 g was dissolved in acetone:methanol (2:5 ratio) mixture and added dropwise to CP3 slurry. After complete addition, the mixture was stirred for additional 1 h and then heated slowly to evaporate the solvent. The solid obtained was dried at 80° C. for 12 h and calcined at 250° C. for 5 h in air. Resultant powder was called as 1% Pd/CP3.

Example 9: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound IA) hydrogenation was carried out in a 50 ml high pressure autoclave. The reactor was charged with 3 g (0.001 mol) compound IA in 15 ml methanol and 0.3 g 1% $Pd/BaF_2$ catalyst as prepared in example 1. The reaction carried out at 60° C. and 5 bar hydrogen pressure for 5 hr. After completion of the reaction, the reaction was analyzed on HPLC (agilent1260 infinity) having C18 column with UV detector (220 nm). The conversion obtained was 100%, and the yield was 99.9%.

Example 10: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound IA) hydrogenation was carried out in a 50 ml high pressure autoclave. The reactor was charged with 3 g (0.001 mol) compound IA in 15 ml methanol and 0.3 g 0.5% $Pd/BaF_2$ catalyst as prepared in example 2. The reaction was carried out at 60° C. and 5 bar hydrogen pressure for 5 hr. After completion of reaction, the reaction was analyzed on HPLC (agilent1260 infinity) having C18 column with UV detector (220 nm). The conversion obtained was 52%, and the yield was 51.5%.

Example 11: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound IA) hydrogenation was carried out in a 50 ml high pressure autoclave. The reactor was charged with 3 g (0.001 mol) compound IA in 15 ml methanol and 0.3 g 1% Pd/HAP1 catalyst as prepared in example 3. The reaction was carried out at 60° C. and 5 bar hydrogen pressure for 5 hr. After completion of reaction, the reaction was analyzed on HPLC (agilent1260 infinity) having C18 column with UV detector (220 nm). The conversion obtained was 95%, and the yield was 94%.

Example 12: Synthesis of tert-butyl 2-(4-(pyridin-2-yl)benzyl)hydrazine-1-carboxylate (IIA)

In a 50 ml two neck round bottom flask was added 0.2 g (0.00066 mol) tert-butyl(Z)-2-(4-(pyridin-2-yl)benzylidene) hydrazine-1-carboxylate (Compound IA), 15 ml methanol and 0.02 g 1% Pd/HAP1 (as prepared in example 3) and heated in an oil bath at 80° C. with hydrogen gas bubbling (15 ml/min) continuously. The reaction was carried out for 18 h till completion of the reaction. After completion of reaction, the reaction was analyzed on HPLC (agilent1260 infinity) having C18 column with UV detector (220 nm). The conversion obtained was 100%, and the yield was 98%.

Example 13: Synthesis of tert-butyl 2-(4-(pyridin-2-yl)benzyl)hydrazine-1-carboxylate (IIA)

In a 50 ml two neck round bottom flask was added 0.2 g (0.00066 mol) tert-butyl(Z)-2-(4-(pyridin-2-yl)benzylidene) hydrazine-1-carboxylate (Compound IA), 15 ml methanol and 0.02 g 1% Pd/BaF2 (as prepared in example 1) and heated in an oil bath at 80° C. with hydrogen bubbling (15 ml/min) continuously. The reaction was carried out for 18 h till completion of the reaction. After completion of reaction, the reaction was analyzed on HPLC (agilent1260 infinity) having C18 column with UV detector (220 nm). The conversion obtained was 100%, and the yield was 96%.

Example 14: Synthesis of tert-butyl 2-(4-(pyridin-2-yl)benzyl)hydrazine-1-carboxylate (IIA)

In a 50 ml two neck round bottom flask was added 0.2 g (0.00066 mol) tert-butyl(Z)-2-(4-(pyridin-2-yl)benzylidene) hydrazine-1-carboxylate (Compound IA), 15 ml Methanol and 0.02 g 1% Pd/HAP1 (as prepared in example 3) and heated in an oil bath at 60° C. with hydrogen gas bubbling (15 ml/min) under atmospheric pressure. The reaction was carried out for 18 hours and analyzed on HPLC (agilent1260 infinity) having C18 column with UV detector (220 nm). The conversion obtained was 90%, and the yield was 87%.

Example 15: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound IA) hydrogenation was carried out in a 50 ml high pressure autoclave. The reactor was charged with 2 g (0.0066 mol) compound IA in 15 ml methanol and 0.2 g 1% Pd/$BaF_2$ catalyst as prepared in example 1. The reaction carried out at 60° C. and 5 bar hydrogen pressure for 5 hr. After completion of the reaction, the reaction was analyzed on HPLC (agilent1260 infinity) having C18 column with UV detector (220 nm). The conversion obtained was 100%, and the yield was 99.9%.

Example 16: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound IA) hydrogenation was carried out in a 50 ml high pressure autoclave. The reactor was charged with 1 g (0.0033 mol) compound IA in 15 ml methanol and 0.1 g 1% Pd/$BaF_2$ catalyst as prepared in example 1. The reaction carried out at 60° C. and 5 bar hydrogen pressure for 5 hr. After completion of the reaction, the reaction was analyzed on HPLC (agilent1260 infinity) having C18 column with UV detector (220 nm). The conversion obtained was 100%, and the yield was 99.9%.

Example 17: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound IA) hydrogenation was carried out in a 1000 ml high pressure autoclave. The reactor was charged with 50 g (0.166 mol) compound IA in 300 ml methanol and 5 g 1% Pd/HAP1 catalyst as prepared in example 3. The reaction carried out at 60° C. and 5 bar hydrogen pressure for 5 hr. After completion of the reaction, the reaction was analyzed on HPLC (agilent1260 infinity) having C18 column with UV detector (220 nm). The conversion obtained was 98%, and the yield was 98%.

Example 18: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound IA) hydrogenation was carried out in a 1000 ml high pressure autoclave. The reactor was charged with 100 g (0.33 mol) compound IA in 500 ml methanol and 10 g 1% Pd/HAP1 catalyst as prepared in example 3. The reaction was carried out at 60° C. and 5 bar hydrogen pressure for 8 hr. After completion of the reaction, the reaction was analyzed on HPLC (agilent1260 infinity) having C18 column with UV detector (220 nm). The conversion obtained was 97%, and the yield was 97%.

Example 19: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound IA) hydrogenation was carried out in a 50 ml high pressure autoclave. The reactor was charged with 0.5 g (0.00166 mol) compound IA in 15 ml methanol and 0.05 g 0.5% Pd/$BaF_2$ catalyst as prepared in example 2. The reaction was carried out at 28° C. and 10 bar hydrogen pressure for 5 hr. After completion of reaction, the reaction was analyzed on HPLC (agilent1260 infinity) having C18 column with UV detector (220 nm). The conversion obtained was 25%, and the yield was 25%.

Example 20: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound A) hydrogenation was carried out in a 50 ml high pressure autoclave. The reactor was charged with 0.5 g (0.00166 mol) compound IA in 15 ml methanol and 0.025 g 1% Pd/HAP1 catalyst as prepared in example 3. The reaction carried out at 80° C. and 7 bar hydrogen pressure for 5 hr. After completion of the reaction, the reaction was analyzed on HPLC (agilent1260 infinity) having C18 column with UV detector (220 nm). The conversion obtained was 85%, and the yield was 85%.

Example 21: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound IA) hydrogenation was carried out in a 50 ml high pressure autoclave. The reactor was charged with 3.0 g (0.01 mol) compound IA in 15 ml methanol and 0.3 g 1% Pd/HAP1 catalyst used in example 11 after washing with methanol and calcining at 400° C. for 5 h. The reaction was carried out at 60° C. and 5 bar hydrogen pressure for 8 hr. After completion of the reaction, the reaction was analyzed on HPLC (agilent1260 infinity) having C18 column with UV detector (220 nm). The conversion obtained was 95%, and the yield was 94%. Thus, catalyst could be recycled efficiently.

Example 22: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound IA) hydrogenation was carried out in a 50 ml high pressure autoclave. The reactor was charged with 0.5 g (0.00166 mol) compound IA in 15 ml methanol and 0.05 g 0.5% Pd/HAP1 catalyst as prepared in example 25. The reaction was carried out at 80° C. and 5 bar hydrogen pressure for 7 hr. After completion of the reaction, the reaction was analyzed on HPLC (agilent1260 infinity) having C18 column with UV detector (220 nm). The conversion obtained was 100%, and the yield was 99%.

Example 23: Synthesis of tert-butyl 2-(4-(pyridin-2-yl)benzyl)hydrazine-1-carboxylate (IIA)

The tert-butyl(Z)-2-(4-(pyridin-2-yl)benzylidene)hydrazine-1-carboxylate (Compound IA) hydrogenation was carried out in a 50 ml high pressure autoclave. The reactor was charged with 0.5 g (0.00166 mol) compound IA in 15 ml methanol and 0.05 g 0.1% Pd/HAP1 catalyst as prepared in example 25. The reaction carried out at 70° C. and 7 bar hydrogen pressure for 7 hr. After completion of the reaction, the reaction was analyzed on HPLC (agilent1260 infinity) having C18 column with UV detector (220 nm). The conversion obtained was 50%, and the yield was 49%.

Example 24: Synthesis of 0.5% Pd/HAP3

Hydroxyapatite (HAP3) (Ca:P ratio 1.3) was synthesized by a co-precipitation method as reported by V. C. Ghantani, S. T. Lomate, M. K. Dongare, S. B. Umbarkar Green Chem., 2013, 15, 1211-1217. In a typical synthesis, the 40.297 g calcium nitrate tetrahydrate and 13.493 g diammonium hydrogen phosphate were dissolved separately in deionised water. Ammonia solution (25%) was added to both the solutions until the pH 7 was achieved. The calcium nitrate solution was added drop wise to the diammonium hydrogen phosphate solution with constant stirring with maintaining pH 7 till complete addition. A thick white precipitate obtained was kept for aging for 12 h and later was filtered, washed with a sufficient amount of water and dried at 120° C. for 16 h. The oven dried solid was calcined in air in a muffle furnace at 600° C. for 4 h which is called as HAP3. Then HAP3 10 g was dispersed in 100 ml water in a 250 ml beaker and stirred to make homogenous slurry. In another beaker Pd(OAc) 0.104 g was dissolved in acetone:methanol (1:3 ratio) and added drop wise to HAP3 slurry. After complete addition, the mixture was stirred for additional 1 h and then heated slowly to evaporate the solvent completely and the solid obtained was dried at 80° C. for 12 h and calcined at 250° C. for 5 h in air. Resultant powder was called as 0.5% Pd/HAP3.

Example 25: Synthesis of 0.1% Pd/HAP3

Hydroxyapatite (HAP3) (Ca:P ratio 1.3) was synthesized by a co-precipitation method as reported by V. C. Ghantani, S. T. Lomate, M. K. Dongare, S. B. Umbarkar Green Chem., 2013, 15, 1211-1217. In a typical synthesis, the 40.297 g calcium nitrate tetrahydrate and 13.493 g diammonium hydrogen phosphate were dissolved separately in deionised water. Ammonia solution (25%) was added to both the solutions until the pH 7 was achieved. The calcium nitrate solution was added drop wise to the diammonium hydrogen phosphate solution with constant stirring with maintaining pH 7 till complete addition. A thick white precipitate obtained was kept for aging for 12 hand later was filtered, washed with a sufficient amount of water and dried at 120° C. for 16 h. The oven dried solid was calcined in air in a muffle furnace at 600° C. for 4 h which is called as HAP3. Then HAP3 10 g was dispersed in 100 ml water in a 250 ml beaker and stirred to make homogenous slurry. In another beaker $Pd(OAc)_2$ 0.022 g was dissolved in acetone:methanol (1:3 ratio) and added drop wise to HAP3 slurry. After complete addition, the mixture was stirred for additional 1 h and then heated slowly to evaporate the solvent completely and the solid obtained was dried at 80° C. for 12 h and calcined at 250° C. for 5 h in air. Resultant powder was called as 0.1% Pd/HAP3

Example 26: Catalyst Recycle Study

The tert-butyl(Z)-2-(4-(pyridin-2-yl)benzylidene)hydrazine-1-carboxylate (Compound IA) hydrogenation was carried out in a 50 ml high pressure autoclave. The reactor was charged with 2 g (0.00166 mol) compound IA in 15 ml methanol and 0.2 g 1% $Pd/BaF_2$ recovered from example 9 by centrifugation and used after drying. The reaction was carried out at 60° C. and 5 bar hydrogen pressure for 5 hr. After completion of the reaction, the reaction was analyzed on HPLC (agilent1260 infinity) having C18 column with UV detector (220 nm). The conversion obtained was 98%, and the yield was 98%.

Advantages of the Invention

Catalyst loading is less

Palladium loading is less (0.1 to 0.01 wt % with respect to substrate)

Milder reaction conditions

Complete conversion (~100%) and formation of product with ~99% selectivity

No need of additional acid or base for hydrogenation.

A cost-effective process

No side products are formed

Efficient catalyst recycle

As 100% conversion is achieved, pure product is obtained without further purification

We claim:

1. A process for hydrogenation of tert-butyl (Z)-2-(4-(pyridin-2-yl)benzylidene) hydrazine-1-carboxylate of Formula IA to tert-butyl 2-(4-(pyridin-2-yl)benzyl) hydrazine-1-carboxylate of Formula IIA, comprising reacting 0.1-2% Pd catalyst on basic support comprising $BaF_2$ or calcium phosphates with Ca/P ratio in a range of 0.76 to 1.8 for the period in the range of 5-18 hours in a solvent at atmospheric pressure up to 20 bar and at a temperature in the range of 25° C. to 100° C. with 1 to 10 wt % catalyst loading with respect to Formula IA to obtain more than 95% conversion of Formula IA and more than 95% of Formula IIA;

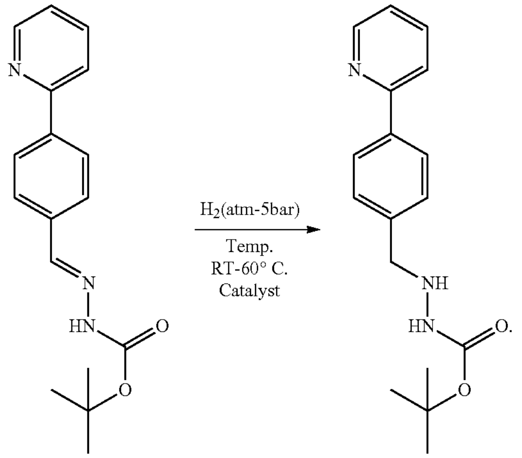
Formula IA Formula IIA
2. The process as claimed in claim 1, wherein the solvent is selected from the group consisting of methanol, iso-propyl alcohol, ethanol, ethylene dichloride, toluene, n-hexane alone and a combination thereof.
* * * * *